(12) United States Patent
Osborne et al.

(10) Patent No.: US 8,277,732 B1
(45) Date of Patent: Oct. 2, 2012

(54) AIR QUALITY DETECTION PACK

(75) Inventors: Michael W. Osborne, Louisville, KY (US); M. Aflal Rahmathullah, Louisville, KY (US); Cheah Wei Ng, Petaling Jaya (MY)

(73) Assignee: AAF-McQuay Inc., Louisville, KY (US)

( * ) Notice: Subject to any disclaimer, the term of this patent is extended or adjusted under 35 U.S.C. 154(b) by 0 days.

(21) Appl. No.: 12/790,759

(22) Filed: May 28, 2010

(51) Int. Cl.
*G01N 21/00* (2006.01)
*G01J 1/48* (2006.01)

(52) U.S. Cl. .......................... 422/83; 422/86
(58) Field of Classification Search .................... 422/83, 422/86
See application file for complete search history.

(56) References Cited

U.S. PATENT DOCUMENTS

| | | | | |
|---|---|---|---|---|
| 4,472,353 A | * | 9/1984 | Moore | 422/401 |
| 4,772,560 A | * | 9/1988 | Attar | 436/165 |
| 5,364,593 A | * | 11/1994 | Mihaylov et al. | 422/87 |
| 5,411,893 A | * | 5/1995 | Eden et al. | 436/165 |
| 6,284,198 B1 | * | 9/2001 | Kirollos et al. | 422/87 |
| 2009/0301381 A1 | | 12/2009 | Robins | |

* cited by examiner

*Primary Examiner* — Lore Jarrett
(74) *Attorney, Agent, or Firm* — Middleton Reutlinger; James E. Cole; John F. Salazar

(57) ABSTRACT

A air gas detection pack is provided. The air gas detection pack has a card receiving pocket which slidably receives a gas detection card, the gas detection card having a plurality of chemically reactive materials retained therein and exposed to outside air through a plurality of aligned air permeable apertures formed in the front and rear wall of the substance detection pack. The combined gas detection card and gas detection pack indicates the concentrations of gases in the air. The air permeable apertures in conjunction with the reactive materials of the substance detection card are covered with a filtering media to protect the reactive material from dirt and dust contamination.

16 Claims, 7 Drawing Sheets

AIR QUALITY DETECTION PACK

TECHNICAL FIELD

The present description is directed generally to a rapid air quality detection pack for providing information on the presence of gases in an airstream or in ambient air, wherein a visual indication of the concentration of an airborne substance is presented through a color-metric chart. Further, described in the various embodiments herein is a rapid, passive detection system using color altering reagents to provide a qualitative and semi-quantitative relation to filtration performance of installed filtration systems.

BACKGROUND

Color reactive papers which have been chemically coated and/or impregnated with a reagent on a base substrate are individually known in the art. These reagent coated/impregnated papers may be utilized to indicate the presence of a particular substance or compound in the air. Gas reactive papers which alter color in the presence of a target gas may be used individually to determine the presence and the concentrations of chemical components present in the air for those that are skilled in reading the color change reaction of the coated paper.

It has been found, however, that these individual chemically reactive papers have a short shelf life or may become fouled or unstable from contaminants such as dust or other materials. Such contamination can make the prior art color reactive papers un-useable for their stated purpose and non-reactive or at least less reactive to their target compound.

Further, chemical and other filtration systems can consist of sorbents such as activated carbon, impregnated activated carbons, zeolites, permanganate impregnated alumina and similar substrates collectively referred to as chemical media. During use, appropriate selected chemical media may remove malodorous, toxic and/or corrosive gases from the environment up to a certain finite life. For determining media change-out schedules, it is typical to estimate what portion of the media has been utilized and by extension when a necessary change-out date is determined. Previously, determination of media exhaustion has been done by coupon analysis (ISA methodology), gas challenge testing (ASTM 6646 or ASHRAE 145.1) and air quality analysis using instrumentation such as gas chromotography/mass spectrometry or gas chromatograph-flame ionization detectors, as well as portable electronic gas sniffers and detectors. A standard for testing remaining usable media capacity may utilize either the ASTM or ASHRAE methods which challenge a small portion of the chemical media with large concentrations of simulated gases in order to predict remaining life. The drawback to such accelerated testing is that it is not representative of contaminant concentrations which may be orders of magnitudes lower in real-life conditions. Lab testing further may not accurately simulate the variety of contaminants in the air in normal field conditions and are known to cross-interact and competitively reside on chemical media. Sophisticated portable electronic instrumentation may not aide in determination of media life due to the cost and time involved in analysis.

SUMMARY

The presently described apparatus and method provides an inexpensive and semiquantitative method of air contaminant analysis using specially coated chemically reactive detection cards. The cards may detect multiple gases, is assembled in a single pack to determine a composite set of gases. The detection pack may have, in various embodiments, a plurality of reactive papers in a card, which, upon exposure to an airstream with a contaminant source, undergoes a color intensity change possibly in proportion to the length of exposure and the concentration of contaminant.

The present disclosure is directed to novel methods and apparatus for detecting foreign compounds in air utilizing an air quality detection pack. More particularly, the present disclosure is directed towards an air quality or gas substance detection pack which has a card receiving pocket formed in the substance detection pack, the card receiving pocket sized to receive a substance detection card, the substance detection card having flow through apertures containing a plurality of chemically reactive papers. The substance detection pack has a plurality of similarly positioned air permeable or air flow apertures which align with the air flow apertures of the substance detection card thereby exposing to ambient air flow the chemically reactive papers positioned and retained within the substance detection card. The substance detection pack has both a front and rear side through which said air permeable apertures are formed and additionally has a filtering media overlaying said plurality of air permeable apertures.

Optionally, the air quality detection pack may have a color coded reaction matrix extending around the periphery of each of the plurality of air permeable apertures or alternatively, around a single air permeable aperture formed in the detection pack. This substance detection pack may further have optional descriptive information regarding substance source charting and chemical material identification allowing the user to locate common origins of typical gases detected.

Generally, in one aspect of the air quality detection pack, the air quality detection pack has a pocket portion, the pocket having a card receiving pocket formed by a front and back card receiving pocket wall. The card receiving pocket has at least one aligned aperture formed in the card receiving pocket front and back wall thus allowing for air to flow through said air quality detection pack. The pack may include, in various embodiments, a filtering media cover which extends at least over the air permeable apertures formed in the substance detection pack. Further the substance detection pack may replacably receive a substance detection card, the substance detection card having at least one air flow aperture which retains therein chemically reactive papers for indication of the presence of substance or gas in the air.

A plurality of chemically reactive papers may be provided optionally in the substance detection card with a matching plurality of air permeable apertures formed in the air quality detection pack.

Optionally, a substance detection card may be provided with a filter media cover extending substantially thereover or extending partially over the substance detection card but effectively covering the chemically reactive papers retained therein to prevent contamination or other fouling. The filter media may be utilized as applications are required for the gas detection pack where high levels of dust are expected thereby requiring protection of the chemically reactive paper strips from contamination. Prevention of such contamination ensures that any color change observed is clearly distinguishable. The gas detection pack may have an air filtration media placed over the chemically reactive papers. The air filtration media may be a expanded-polytetrafluoroethylene (ePTFE) filtering media used for the purpose of allowing contaminated air to pass through the media while preventing dust particles to permeate. The ePTFE media may be a spunbond scrim product held in place by a non-outgassing adhesive.

In some embodiments, the gas detection pack has a plurality of air permeable apertures, each of said air permeable apertures representative of a particular gas compound, the plurality of air permeable apertures filled with corresponding chemically reactive papers which change color in the presence of such gas compounds. A color code reaction matrix wheel may be placed around the periphery of the plurality of air permeable apertures indicative of the color change expected when said chemically reactive paper is in the presence of said specific target compounds. In some embodiments a removable substance detection card is not needed. Further, the substance detection pack may have a complete or at least substantial covering of filtering media extending over each of the air permeable apertures and hence the chemically reactive paper in order to protect the chemically reactive materials from dirt and dust contamination.

In various embodiments, the gas compounds which are tested by the air quality detection pack may include ammonia, chlorine, hydrogen sulfide, nitrogen oxide, sulfur dioxide, ozones or aldehydes, mercaptans, etc.

In other embodiments the filtering media may extend entirely over the card receiving pocket of the substance detection pack.

In some embodiments the filtering media may extend only partially over the exterior walls of the card receiving pocket of the substance detection pack.

In even further embodiments, the filtering media may extend partially or entirely over a substance detection card wherein the substance detection card may have a single or a plurality of chemically reactive materials retained therein.

In some embodiments, the substance detection pack may only have a singular air permeable aperture for alignment with a singular chemically reactive paper positioned on a substance detection card.

In various embodiments, the substance detection pack may be placed both upstream and downstream of an air handling unit that has a chemical filtration system and would quickly provide information on whether a contaminant is present in the air stream as well as approximate concentrations. Further, use of the gas detection pack may include placement of detectors upstream and downstream of the chemical media which would quickly allow a user to determine if contaminants are present which are not being removed by the media.

It should be appreciated that all combinations of the foregoing concepts and additional concepts discussed in greater detail below (provide such concepts are not mutually inconsistent) are contemplated as being part of the invented subject matter disclosed herein. In particular, all combinations of claimed subject matter appearing at the end of this disclosure are contemplated as being part of the inventive subject matter disclosed herein. It should also be appreciated that terminology explicitly employed herein might also may appear in any disclosure incorporated by reference should be accorded a meaning most consistent with the particular concepts set forth.

BRIEF DESCRIPTION OF THE DRAWINGS

From the drawings, like reference characters generally refer to the same parts throughout the different views. Also, the drawings are not necessarily to scale, emphasis instead generally being placed upon illustrating the principles set forth in this disclosure.

DETAILED DESCRIPTION

Figure 1:
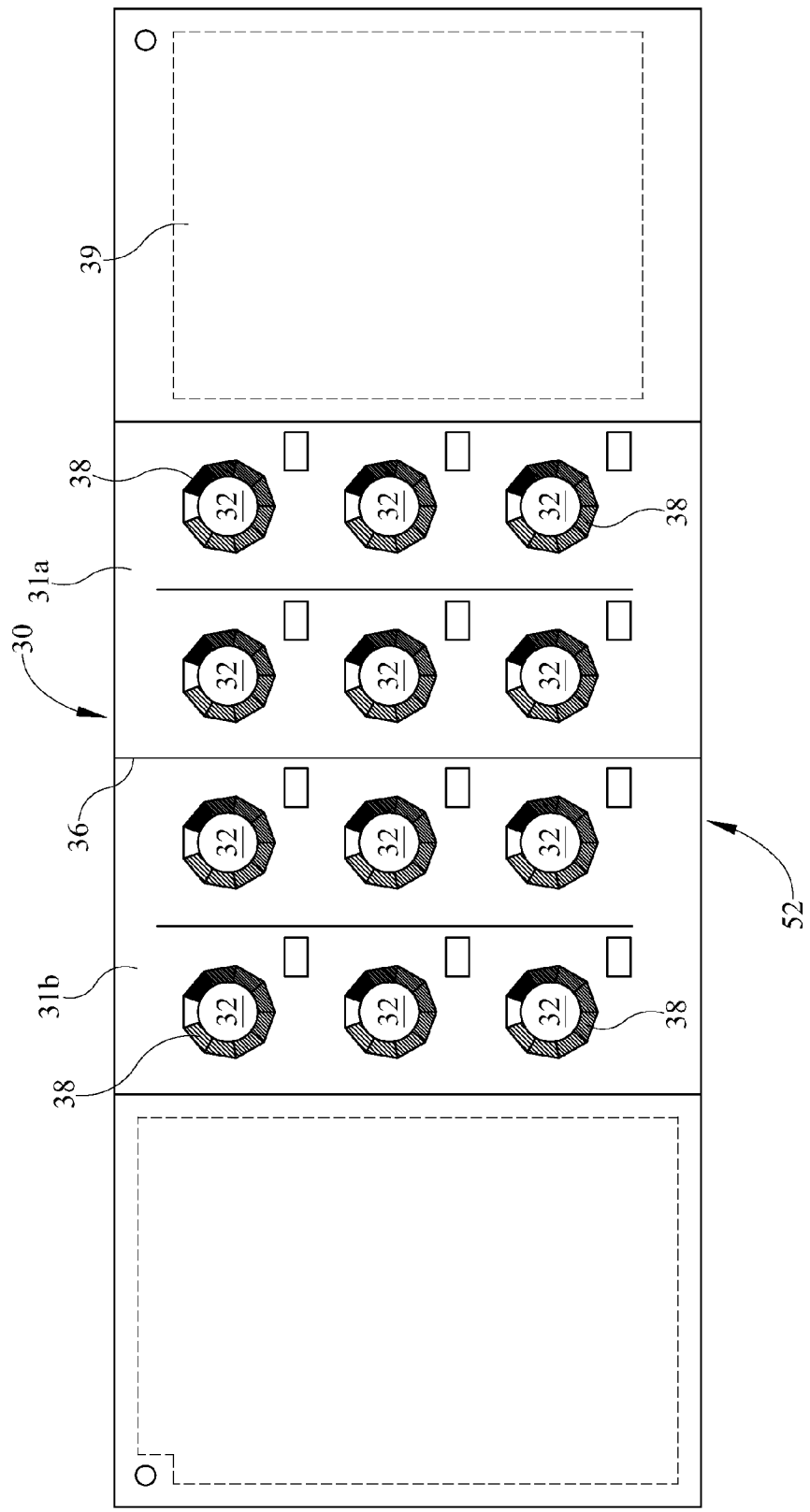
FIG. 1 illustrates a flat planar view of the unfolded substance detection pack blank described herein.

In the following detailed description, for purposes of explanation and not limitation, representative embodiments disclosing specific details are set forth in order to provide a thorough understanding of the claims. However, it will be apparent to one having ordinary skill in the art and having had the benefit of the present disclosure that other embodiments according to the present teachings that depart from the specific details disclosed herein remain within the scope of the appended claims.

Moreover, descriptions of well known apparatuses and methods may be omitted so as not to obscure the description of the representative embodiments. Such methods and apparatuses are clearly within the scope of the claims. For example, the embodiment of the substance detection pack set forth in the figures is shown having a pre-defined number of air permeable apertures and a pre-defined location of the filtering media. Accordingly, for illustrative purposes, the claims are to be considered in conjunction with such construction. However, other pack configurations that incorporate the filtering media over a reactive material on a substance detection card and/or a substance detection pack having a card receiving pocket, among others, are contemplated without deviating from the scope or spirit of the claimed invention. Further, the reactive material may be of various known reactive types, including chemically, absorption or any other process which would provide an indication on the substrate of the presence of the challenged or targeted gas.

The air quality detection pack described herein provides information on the presence of gases in ambient air or in an airstream. Such detection pack provides an easy visual indication of the presence of a target compound and an estimate of the gas concentrations that can be used to evaluate the need for gas phase filtration equipment, estimating filter efficiency or additional building and air filtering requirements. The air quality detection pack presently described utilizes chemically reactive materials that change colors through reaction with gas contaminants in the air. The color and extent of color change depends on the concentration of the gas and the exposure time. By knowing the correlation of reaction paper color to ppb-hr (i.e. parts per billion concentration×hours of exposure time) concentrations and the amount of time the chemically reactive paper that is exposed to the air, a concentration of the substance can be estimated. Target gas concentrations in parts per billion may be roughly calculated by dividing the average exposure range in ppb-hr by the exposure time in hours.

Thus, if an exposure time of two hours is provided and exposure range of 125 to 250 parts per billion per hour of hydrogen sulfide ($H_2S$) is detected, a calculation of parts per billion concentration may be made as $$\frac{125 \text{ ppb}}{2 \text{ hours}} - \frac{250 \text{ ppb}}{2 \text{ hours}}$$

Such estimates may provide a resulting calculation range equal to 63-125 ppb of $H_2S$. Further, testing and correlative analysis can provide color charting for each type of reagent in terms of ppb/hr such that standardized color charting and reactivity of the paper can be properly estimated using known correlations of paper color to ppb-hr. For example, testing may indicate that in low ppb-hr values, differences in reaction rates and hence color changes may be substantially equivalent irrespective of target or challenge gas concentrations. The difference may rapidly become larger as the ppb-hr value increases. This would suggest that although the reagent papers can be utilized as a rapid and qualitative indicator, the reagents may be considered semi-quantitative with about a +/−25 ppb standard deviation only up to a maximum of 300 ppb-hr.

The air quality detection pack described herein may be utilized in various potential locations including outdoor air intakes, upstream and down stream of gas phase filters, inside protected or critical air spaces or at the outlet of odor scrubbers. Such locations may provide valuable information regarding gas presence, gas concentration and gas phase filter performance.

Figure 5:
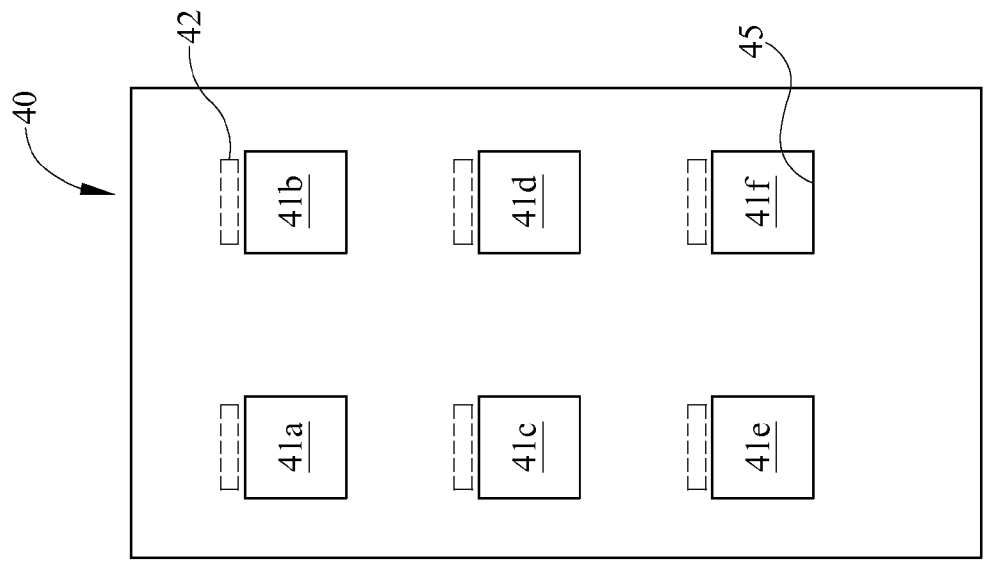
FIG. 5 is a front planar view of the substance detection card which is insertable into the folded substance detection pack of the present invention.

As shown in FIG. 1, a flat planar view or blank view of the substance detection pack is presented wherein the substance detection pack 30 has a fold line 36 which bifurcates the pack as shown. Depicted in FIG. 1 is both the front and rear surface of the substance detection pack in combination with a plurality of air permeable or flow through apertures 32. Each of the air permeable apertures is representative of a particular chemical substance which is detected by a correspondingly positioned chemically reactive paper 41a-41f located within a substance detection card 40, shown in FIG. 5 or positioned in each aperture 32. Each of the air permeable apertures 32 may be peripherally surrounded by a color code reaction matrix 38 which is indicative of the color change of the chemically reactive paper at various concentrations when in the presence of an identified chemical composition or component. The color code reaction matrix may be calibrated for the specific system presently described used in conjunction with the filtration media implemented as the effect of using ePTFE or other filtration media may slightly alter the color change.

Figure 2:
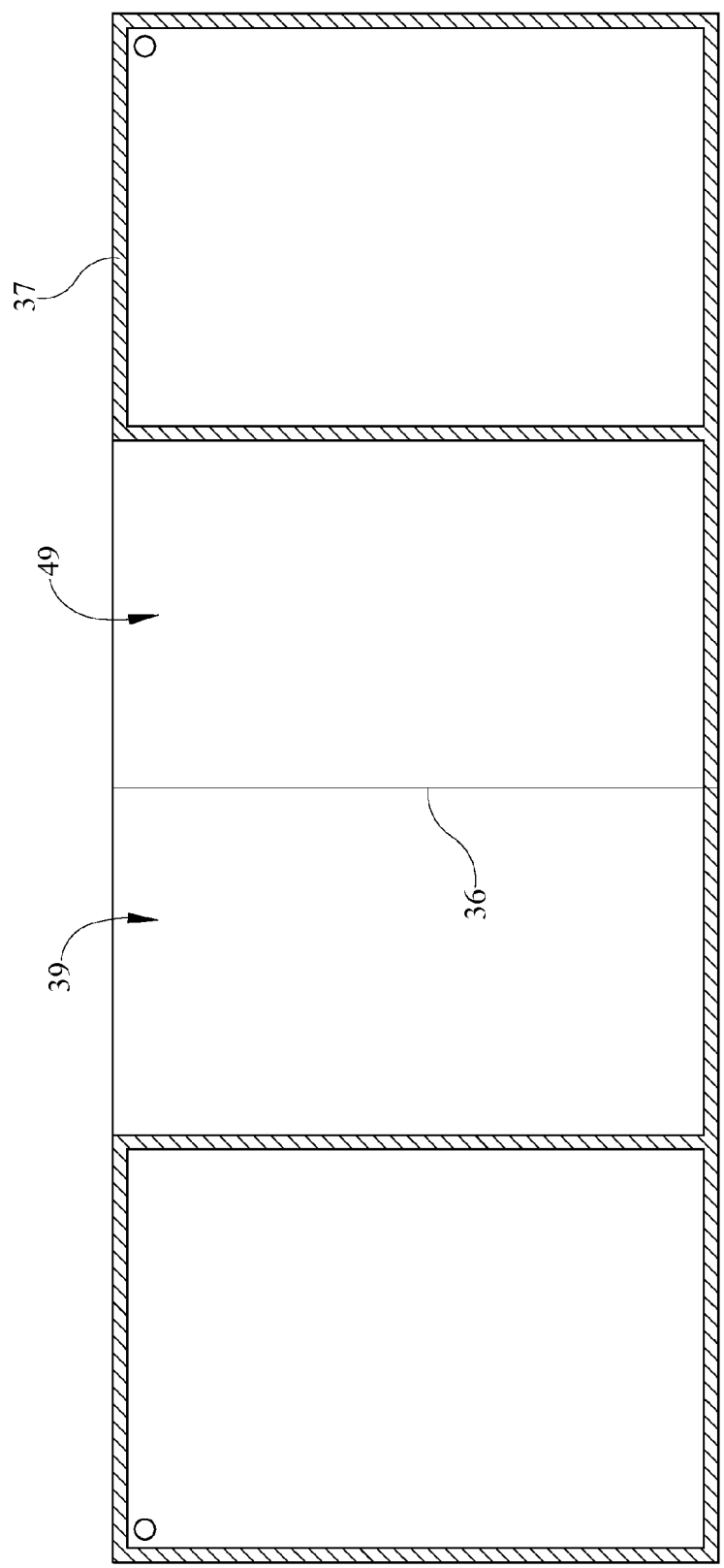
FIG. 2 illustrates the opposing side of the flat planar view of the substance detection pack of FIG. 1.
Figure 3:
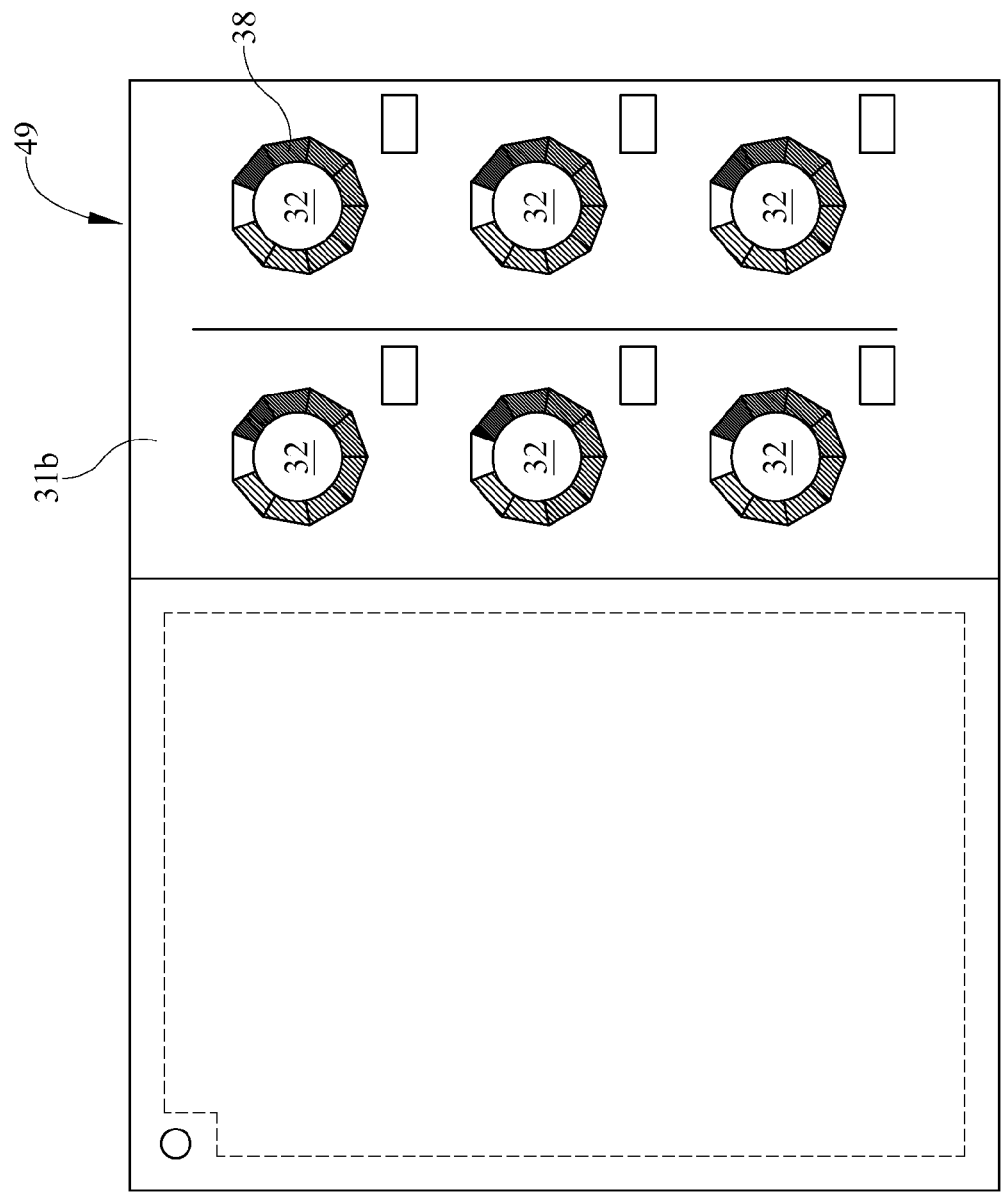
FIG. 3 illustrates a rear view of the folded substance detection pack of the present invention.
Figure 4:
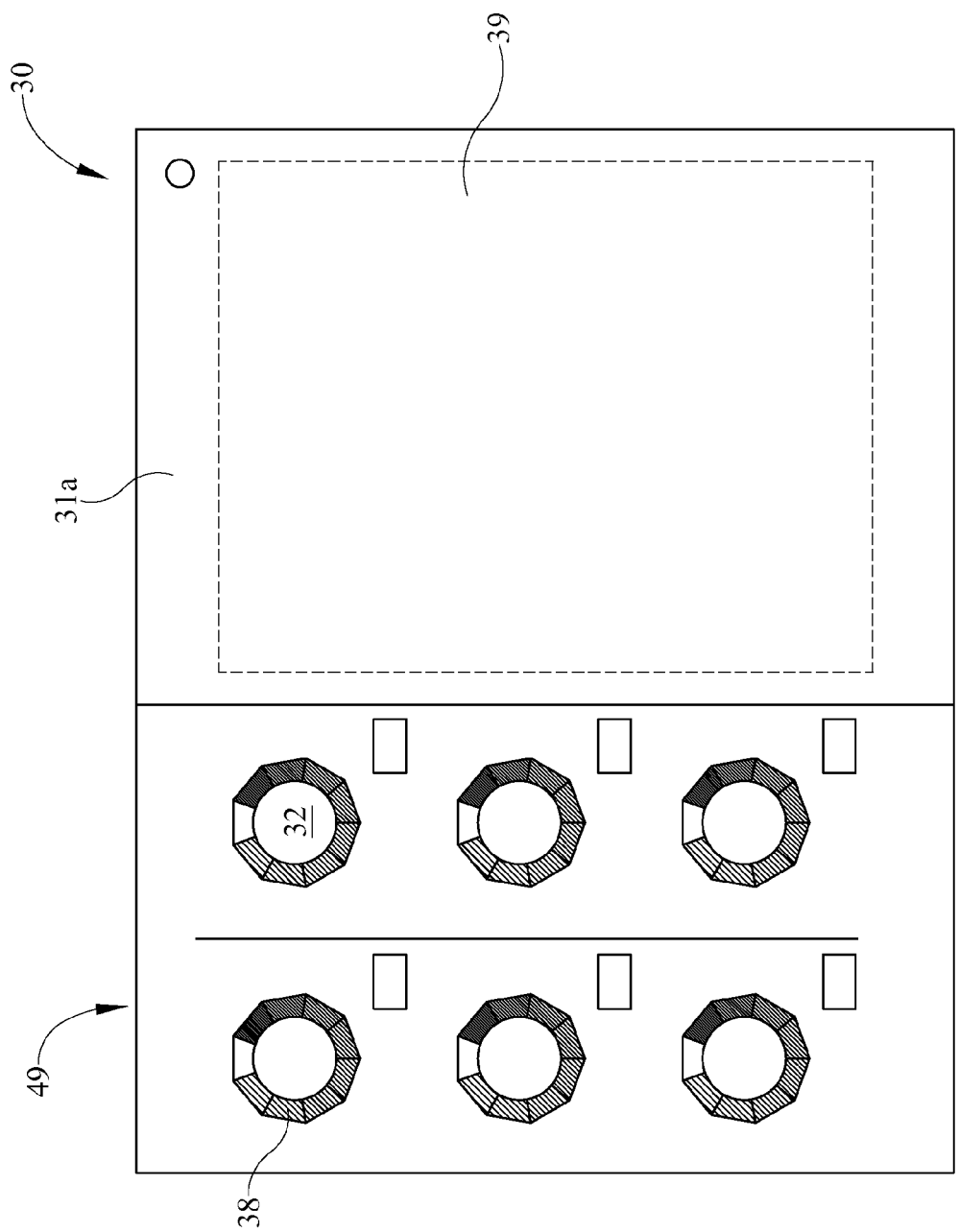
FIG. 4 depicts a front view of the folded substance detection pack of the present invention.

The substance detection pack 30 shown in FIG. 1 has both a front wall 31a and a rear wall 31b which are adhered together after folding along fold line 36 along the adhesive lines 37 depicted in FIG. 2. Upon placement of adhesive or other mechanical affixation mechanism to retain the front wall 31a in close abutment with the rear wall 31b, a card receiving pocket 49 may be formed by three separate walls, an adhesive side wall, fold line 36 and an adhesive bottom wall 52. Upon folding of the substance detection pack at the fold line 36, both front and back surfaces 31a, 31b may be permanently adhered together with the card receiving pocket 49 available for slidably receiving a substance detection card 40 shown in FIG. 5. Front and rear walls 31a and 31b of the pack 30 provide the ability to visually gauge in the presence and concentrations of a target gas detected by the substance detection card through comparison to color code reaction matrices 38. The color code reaction matrices 38 surround each of the air permeable apertures 32 to provide estimated concentrations in parts per billion or other desirable concentrations, to the user.

The air permeable apertures 32 extend through the substance detection pack 30 thereby allowing air flow and exposing the correspondingly positioned chemically reactive papers 41a, 41b, 41c, 41d, 41e and 41f for chemical interaction. Each of the chemically reactive materials may further be labeled with a substance label 42 indicating the substance or compound being detected by the particular reactive paper. The substance detection card 40 may be designed as is well known in the art to be insertable in only one orientation or, alternatively, the substance labels 42 may be readily apparent and matching the various labels positioned around the air permeable apertures 32 on the substance detection pack 30 and on the card 40. Thus, proper orientation of the card 40 into the pocket 49 may be readily achieved.

The card 40 may have a plurality of firmly retained papers or substrates with reagents 41a-41f, each impregnated with a specific chemical material. The chemical material impregnating the paper is chosen to react with a target gas and change color according to known base line standards. Such known color change standards may be represented in the individual color matrices shown around each aperture.

It is preferable to protect each gas detecting reagent paper combination as they can react differently as a result of inconsistencies in the tape, degradation over time, water vapor, cross contamination and dirt and dust fouling. Thus it is desirable to protect such substrate bearing material and reagent during shipment, storage, and in use. Filter media 20 may be made of known non-woven layer material/media which will sufficiently protect the impregnated substrate material 41a-41f, allow contact of the target gas with the paper and allow visual verification of the matrices 38 if needed or desired.

Upon insertion of the substance detection card 40 into the card receiving pocket 49 formed in the substance detection pack, the plurality of chemically reactive papers 41a-41f may be correspondingly aligned with the appropriate air permeable apertures 32 labeled on the front or rear wall 31a, 31b of the substance detection pack.

As an example, the substance detection card 40 may have similarly constructed front and rear labels 42 and may have chemically reactive papers for such gases as ammonia, chlorine, hydrogen sulfide, nitrogen dioxide, sulfur dioxide and ozone. However, these are only exemplary descriptions and target gases which may be detected utilizing the herein described substance detection pack and card combination.

Further, to aid in interpretation of the various color changes depicted, a substance source chart 39 may be provided which may indicate the possible originating source of the gas in a matrix of source and gas presence combinations. Thus, for example, it may be apparent that diesel combustion may be correspondingly the cause of nitrogen dioxide, ozone and/or sulfur dioxide and thus tied to the presence of such gas. For example, the substance source chart 39 may be in matrix format, each of the substances listed in the substance labels 42 placed in combination with typical sources for each of said substances. For example, various exhausts, operations and other mechanical devices which emit such sources may be listed so that a user may readily ascertain potential sources for gases found through the air quality detection system presented herein.

Recommended exposure time of the chemically reactive paper in the substance detection card to the airstream is preferred to be between two and 24 hours. In low concentration environments, it is expected that the longer residence times may be utilized.

Color reactive papers 41a-41f may be utilized in the card 40. Such papers may be, for example, substrate papers bearing material which reacts with target gases, such as Honeywell Analytics Midas® sensor cartridge materials.

Returning to FIG. 1, the substance detection pack 30 of the various embodiments is depicted in planar form, wherein the front wall 31a and rear wall 31b are disclosed. The material of the substance detection pack 30 may be, for example, paper board capable of mechanical folding along fold line 36. Further, as depicted in FIG. 2 and in conjunction with the front view of FIG. 1, adhesive material may be applied as shown along adhesive line 37 utilizing various known adhesive methods. However, care must be taken in the implementation for adhering both front and back faces in using a material which does not emit contaminants. Further, adhesive material may be replaced with other known adhesive mechanisms which are known in the art.

Card receiving pocket 49, as shown in the various embodiments, may be formed by keeping the top portion of the pocket unadhered so that the formed pocket after mechanical adhesion of the front and back walls of the substance detection package may slidably receive a substance detection card 40. The card receiving pocket may be sized so that the substance detection card may readily fit within the formed pocket 49. Further, pocket 49 should be sized appropriately so that the air flow apertures 32 align properly with the plurality of singular chemically reactive papers 41a-41f retained in the substance detection card 40.

Figure 6:
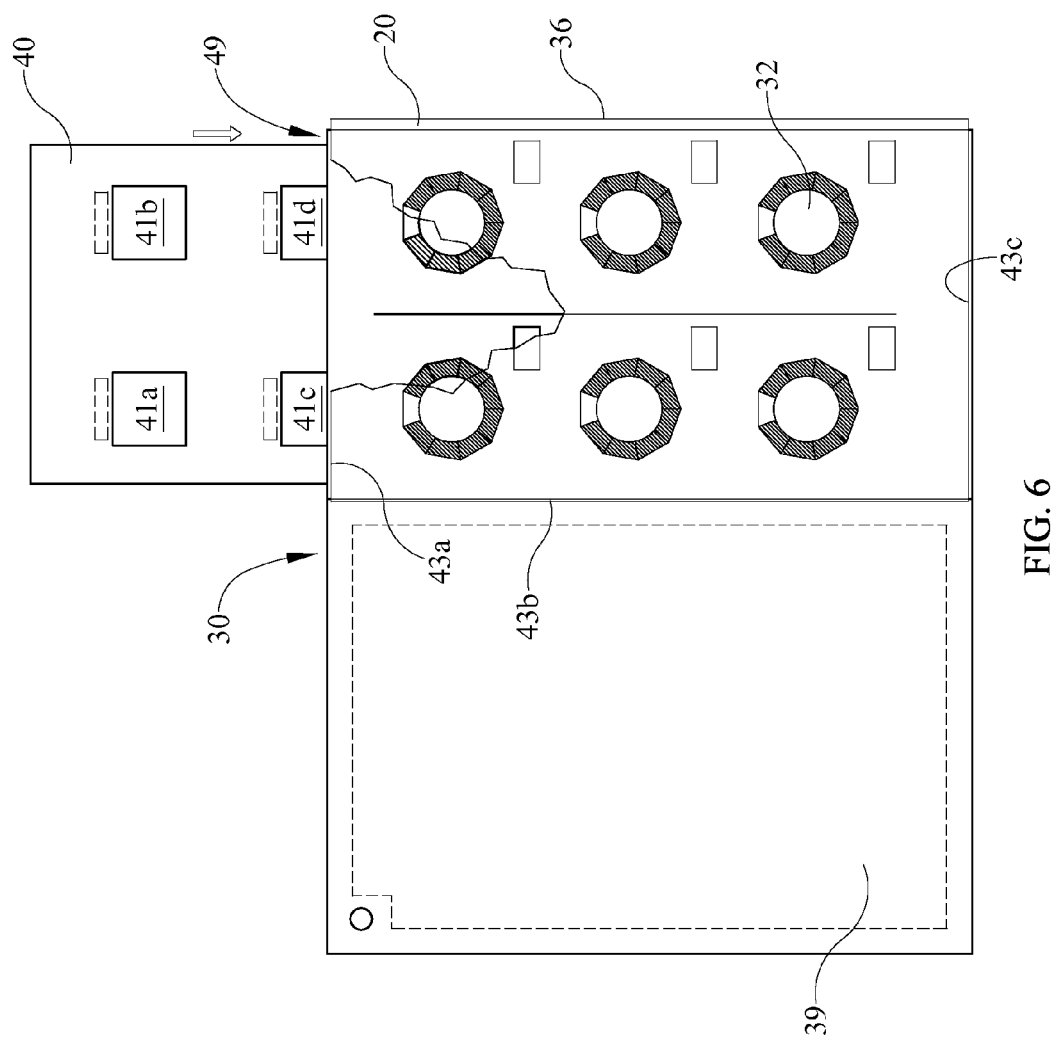
FIG. 6 is a partial installed view of the substance detection card partially installed in the folded substance detection pack of the present invention.

Returning to FIG. 6, substance detection card 40 may be inserted into the formed pocket 49 of the detection pack 30. In utilizing the substance detection card and chemically reactive paper in an airstream or in ambient air, minimization of dust exposure and other contaminates is preferred. Also shown is a layer of filtering media 20 which extends, in this depicted embodiment, over the front and rear wall of the pocket 49 such that the air permeable apertures 32 are properly covered thereby protecting the chemically reactive papers 41a-41f from dust and dirt contamination. In the depicted embodiment, filtering media 20 may extend from approximately the fold line 36 which forms the right edge of the pocket 49 to the beginning of the substance source chart 39. Filtering media 20 may be adhered to the detection pack 30 along filter media edges 43a, 43b and 43c and similarly adhered on the opposite side such that it is firmly retained in place and fully encases and overlays the air permeable apertures 32 on both the front and rear surfaces to properly seal them from contamination. By properly adhering on both the front and rear surface of the substance detection pack 30 along edges 43a, 43b and 43c, contaminants and other materials may be prevented from becoming interposed between the filtering media 20 and reactive papers 41a-41f of the detection card 40. It may also be desirable that filtering media 20 as shown in the embodiment of FIG. 6, be visually permeable such that the gas labels and color reaction matrix 38 of the detection pack 30 is viewable.

Filtering media 20 may alternatively be a filter media layer placed upon or over air permeable apertures 32 as opposed to a long continuous filtering media adhered in place as depicted. Such embodiments and modifications are well understood by one of ordinary skill in the art having the benefit of the present disclosure.

Filtering media 20 may be made of a spunbond scrim such as the following polypropylene scrim material having the following characteristics:

TABLE 1

| Item | UOM | Unit | Standard |
|---|---|---|---|
| Color | NA | White | NA |
| Material | NA | PP | NA |
| Technology | NA | spun bond | NA |
| Basic Weight | g/m2 | 20 ± 5 | NA |
| Thickness | mm | 0.20 ± 0.15 | GB/T3820-1997 |
| Permeability | cfm | >1000 | ASTM D737 |
| Tensile Strength | N/5 cm | MD > 25 CD > 15 | GB/T3923.1-1997 (clamping distance 20 cm, pulling speed 20 cm/min) |

Various known filter media 20 may be implemented to protect the substance detection card 40 and the various chemically reactive papers retained therein. Filtering media 20 may be provided to minimize dust, dirt and other contaminant exposure. Thus, a layer of filter media to protect the card 40 is provided in various embodiments. Variations may be provided for in the thickness and permeability of the membranes. The higher permeability of the media may allow for more airflow and thus better diffusion and contact between the colorimetric paper and contaminant of interest.

Filtering media 20 may be selected from various known media which allow diffusion of the various gases therethrough. Thus, known synthetic media which inhibits such diffusion of gas phase contaminates such as hydrogen sulfide, chlorine and others which would prevent contact of such gas phase materials with papers 41a-41f should be avoided. Any other alternative filtering media which would not affect the reaction of chemical paper materials may be utilized.

Further, it may be desirable to separate the substance detection pack 30 and card 40 during shipping and storage due to cross contamination. Further, sufficient separation of papers 41a-41f must occur due to possible cross-migration of solvents, between papers which can cause interference and false positives.

Figure 7:
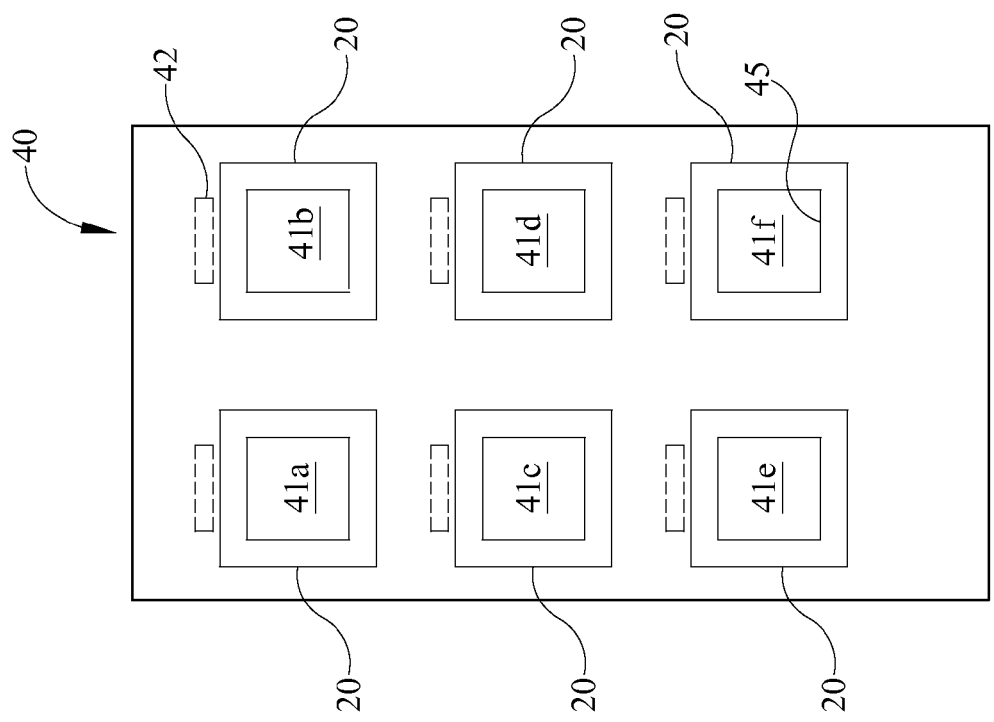
FIG. 7 is an alternative embodiment of the substance detection card as described herein.

Alternatively, as depicted in FIG. 7, a further embodiment is shown in which the individual substance detection card 40 is depicted, each of the air flow aperture peripheries 45 defining the boundary of a chemically reactive paper 41a-41f, the peripheries each covered with a protective filtering media 20 on both a front and rear surface such that air may flow through the air permeable aperture 32 of the substance detection pack 30 and allow potential gases intrained within the air to contact the chemically reactive papers 41a-41f such that they may react properly and discolor as required to indicate concentrations within the airstream. Such an embodiment removes the requirement of having a separate substance detection pack and pocket part.

Alternatively, in a further embodiment, the substance detection pack 30 may be manufactured with integrated chemically reactive materials 41a-41f adhered along an inner surface of the pack 30 and within the air permeable apertures 32. In such an embodiment, each of the individual reactive materials 41a-41f may be fully encased within the pack 30 and the pack 30 may be then fully sealed with a full or partial filter covering 20 extending thereover. Such variations of embodiments depicted are felt to be incorporated within the disclosure presented herein.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein.

More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. An air quality detection package, comprising:
a pocket pack, said pocket pack having a card receiving pocket formed by a front and a back receiving pocket wall and an opening along an edge of said pocket pack extending into said card receiving pocket, said card receiving pocket having at least one aligned aperture formed in said card receiving pocket front and back wall;
a gas detection card, said gas detection card sized to removably fit within said card receiving pocket and having at least one chemically reactive material retained in said card, said material exposed on both a front and a back surface of said card, said chemically reactive material of said card being substantially aligned with said at least one aperture of said card receiving pocket front and back wall; and
a filtering media sealingly extending over said at least one aligned aperture of said front and back wall of said card receiving pocket.

2. The air quality detection package of claim 1 wherein said filter media is visually permeable.

3. The air quality detection package of claim 2 wherein said filter media extends over said front and back receiving pocket wall.

4. The air quality detection package of claim 1 wherein said gas detection card has a plurality of chemically reactive materials and wherein said card receiving pocket has a matching plurality of aligned apertures.

5. The air quality detection package of claim 4 wherein said plurality of chemically reactive materials are color indicative of the presence of a plurality of different gases.

6. The air quality detection package of claim 4 wherein said plurality of chemically reactive materials align with said matching plurality of said aligned apertures.

7. The air quality detection package of claim 6 wherein each of said plurality of said aligned apertures of said card receiving pocket are peripherally lined with a color code reaction matrix indicative of a concentration level of a gas.

8. The air quality detection package of claim 1 wherein said gas detection card is removable from said pocket pack.

9. An air quality indicator package, comprising:
a gas detection kit having a pocket part for removably a substance detection card, said pocket part having an opening along an edge wherein said detection card is received;
said pocket part having at least one air flow through pathway;
said at least one air flow through pathway aligned with a reactive material affixed on said substance detection card; and
said pocket part air flow through pathway sealingly covered with a filtering media to protect said reactive material on said substance detection card.

10. The air quality detection package of claim 9 wherein said pocket part of said gas detection kit is substantially surrounded by said filtering media.

11. The air quality detection package of claim 9 wherein said pocket part of said gas detection kit has a front and a back wall open along a top wall and slidably receives said substance detection card through said open top wall.

12. An air flow gas detection pack, comprising:
a gas detection card having a plurality of chemically reactive papers embedded within said card;
a gas detection card receiving pack having a slide pocket, said slide pocket sized to removably receive said gas detection card along at least one open side of said slide pocket;
wherein said slide pocket of said detection card receiving pack has a front and a back wall with a plurality of aligned air flow apertures;
said aligned air flow apertures of said detection card receiving pack aligned with said plurality of reactive papers in said gas detection card when said card is inserted in said slide pocket; and,
a filtering media extending substantially over said air flow apertures of said slide pocket of said detection card receiving pack.

13. The air flow gas detection pack of claim 12 wherein said slide pocket is formed from three closed sides and said one open side, said one open side capable of slidably receiving said gas detection card.

14. The air flow gas detection pack of claim 13 wherein said gas detection card is slidably removable from said slide pocket and frictionally retained in place within said pocket.

15. The air flow gas detection pack of claim 12 wherein said detection card receiving pack includes color code reaction levels surrounding said plurality of air flow apertures.

16. A substance detection card pack, comprising:
a pocket part having a plurality of air flow apertures, said pocket part having an opening along at least one edge;
said opening receiving a removable card having at least one gas reactive material, each of said air flow apertures aligned with said at least one gas reactive material, said at least one gas reactive material color indicative of a target substance present in airstream; and,
a filtering media substantially covering each of said airflow apertures to protect said at least one gas reactive material from dirt and dust contamination wherein said filtering media is a spun bond polypropylene scrim material with a basis weight of between about 15 to 25 g/m2; a thickness of about 5 to 35 mm.

* * * * *